United States Patent [19]

Widmer et al.

[11] 3,960,966

[45] June 1, 1976

[54] KETOISOPHORONE MANUFACTURE

[75] Inventors: Erich Widmer, Munchenstein, Switzerland; Marcel Seuret, East Brighton, Victoria, Australia

[73] Assignee: Hoffmann-La Roche Inc., Nutley, N.J.

[22] Filed: June 19, 1975

[21] Appl. No.: 588,274

[30] Foreign Application Priority Data

June 28, 1974 Switzerland.......................... 8927/74
May 27, 1975 Switzerland.......................... 6747/75

[52] U.S. Cl............................................. 260/586 P
[51] Int. Cl.$^2$........................................... C07C 45/00
[58] Field of Search................................. 260/586 P

[56] References Cited
FOREIGN PATENTS OR APPLICATIONS
2,356,546    5/1974    Germany.......................... 260/586 P

OTHER PUBLICATIONS

Wada, "Chem. Pharm. Bull." (Tokyo), vol. 13(1), pp. 43–49 (1965).

Wada "Chem. Pharm. Bull." (Tokyo), vol. 12(9) pp. 1117–1118 (1964).

Hawkins, "J. Chem. Soc." 1955, pp. 3288–90.

*Primary Examiner*—Norman Morgenstern
*Attorney, Agent, or Firm*—Samuel L. Welt; Bernard S. Leon; Richard A. Gaither

[57] ABSTRACT

A process for the manufacture of ketoisophorone by the oxidation of $\alpha$-isophorone employing oxygen gas in the presence of a catalyst.

10 Claims, No Drawings

3,960,966

KETOISOPHORONE MANUFACTURE

BACKGROUND OF THE INVENTION

Ketoisophorone, as presently prepared, has several disadvantages, for example, inefficient conversion of starting material resulting in the presence of a considerable amount of starting material at reaction's end. Furthermore, undesirable by-products are obtained.

SUMMARY OF THE INVENTION

The present invention is concerned with a process for the manufacture of ketoisophorone.

According to the present invention, ketoisophorone (3,5,5-trimethyl-2-cyclohexen-1,4-dione) is manufactured by oxidizing α-isophorone (3,5,5-trimethyl-2-cyclohexen-1-one) with an oxygen-containing gas in the presence of catalytic amounts of phosphomolybdic acid, silicomolybdic acid or a salt thereof, or of molybdenum (VI) dioxybisacetylacetonate, vanadium (IV) dichlorobisacetylacetonate or vanadium (V) oxydichloromonoacetylacetonate.

DETAILED DESCRIPTION OF THE INVENTION

The preparation of ketoisophorone according to the instant invention offers several advantages over methods known heretofor. For example, α-isophorone is practically completely converted to ketophorone in a one-stage process. This allows for quantitative removal of the ketoisophorone from the oxidation mixture. The separation of the ketoisophorone from the volatile by-products is accomplished in a simple manner whereas separation of the material prepared according to prior art processes is quite difficult due to the presence of a considerable amount of the starting material.

The phosphomolybdic acid, silicomolybdic acid (or salts thereof), molybdenum (VI) dioxybisacetylacetonate, vanadium (IV), dichlorobisacetylacetonate or vanadium (V) oxydichloromonoacetylacetonate are well known materials which are readily available and inexpensive.

As salts of phosphomolybdic acid and silicomolybdic acid which can be used in the present process, the alkali metal salts, such as the sodium and potassium salts are particularly preferred. The corresponding ammonium salts are preferred.

As a particularly preferred embodiment of the present process, there is used a catalyst composition which contains, in addition to the above-mentioned catalysts one or more of the following catalyst additives: a copper-(II) salt, especially copper sulfate, or copper citrate, copper acetate or copper naphthenate, cer-(III)-acetylacetonate, molybdenum, trioxide, palladium, an alkali metal dichromate or tungstic acid. The advantage of using these catalyst additives results in a further increase in the yield of the desired ketoisophorone.

The catalyst additive can be used in amounts of about 2 wt.% to about 50 wt.%, especially about 2 wt.% to about 20 wt.%, for example about 2 wt.% to about 15 wt.%, based on the total amount of catalyst (i.e., actual catalyst substances plus catalyst additive).

Examples of mixed catalysts containing such catalyst additives are phosphomolybdic acid and molybdenum trioxide, copper sulphate, copper citrate, copper naphthenate, palladium, potassium dichromate, cer-(III)-acetylacetonate or tungstic acid, for example, in a ratio of 98:2 wt.% up to a ratio of 50:50 wt.%.

The aforementioned catalyst additives can be used singly or in admixture. Examples of an individual catalyst substance with two catalyst additives are mixtures of phosphomolybdic acid and copper sulphate plus molybdenum trioxide, e.g., in the ratio of 80:10:10 wt.%, or of copper sulfate plus tungstic acid, e.g., in the ratio of 80:15:5 wt.%, or of copper sulfate plus copper citrate, e.g., in the ratio of 50:40:10 wt.%, or of copper sulfate plus palladium, e.g., in the ratio of 80:15:5 wt.%, or of copper sulfate plus cer-(III)-acetylacetonate, e.g., in the ratio of 90:5:5 wt.%.

The amount of catalyst used can lie between about 0.1 wt.% and 10 wt.%, preferably between 0.5 wt.% and 4 wt.%. The use of about 2 wt.% of catalyst is especially preferred. These amounts are in each case based on the amount of α-isophorone used.

The oxidation of α-isophorone in accordance with this invention can be carried out in the absence of, or in the presence of an inert solvent. It is preferred to carry out the oxidation in the absence of a solvent. When the oxidation is carried out in the presence of a solvent, the preferred solvents are halogenated hydrocarbons such as monochlorobenzene, dichlorobenzene, bromobenzene, benzyl chloride, dibromobenzene, benzal chloride and the like. Alkylated aromatic solvents such as toluene, xylene, ethylbenzene, cumene, naphthalene and the like.

As the oxygen-containing gas, there can be used, for example, pure oxygen or air, the use of air being preferred.

The amount of air or oxygen-containing gas passed through the batch of reactants per unit time can vary. In the case of 50 g. batches, between about 25 and 500 ml. per minute, especially between about 50 and 200 ml. per minute is passed through. In general, the time required to complete the oxidation amounts to about 24–100 hours depending on the size of the batch, the amount of catalyst used, the temperature and the air-flow velocity.

The oxidation is expediently carried out at a temperature between about 50°C. and 150°C. A preferred temperature range for carrying out the oxidation lies at between about 80°C. and 100°C.

The slag remaining after the separation of the ketoisophorone can be combusted and the combustion residue processed to fertilizer.

Ketoisophorone is, as is well known, an important intermediate in the manufacture of vitamin E, of various carotenoids and odorants.

The present process can be carried out continuously or batchwise.

The following examples illustrate the present invention.

EXAMPLE 1

500 g. of α-isophorone and 10 g. of phosphomolybdic acid in a 1500 ml. of sulfonation flask provided with a stirrer, gas delivery frit, thermometer and reflux condenser are heated to 100°C. in an oil with continuous stirring. In so doing, air is continuously blown through the glass frit into the mixture. The initially green-blue solution takes on a dark-olive color during the course of several hours and shows a slightly increased viscosity.

After an oxidation time of 95 hours, 98.5% of the starting material is converted. The mixture is smoothly distilled to give 308 g. of a yellow distillate which, apart from volatile and unknown oxidation products, contains mainly ketoisophorone. The yield of ketoisophorone is 45%; purity: 80–90%.

The crude product can be purified by fractional distillation with a Fenske ring column, ketoisophorone of 98–100% purity being obtained.

EXAMPLE 2

When the procedure described in Example 1 is carried out using silicomolybdic acid, molybdenum VI dioxybisacetylacetonate, vanadium IV dichlorobisacetylacetonate or vanadium V oxydichloromonoacetylacetonate instead of phosphomolybdic acid, there is likewise obtained a conversion of almost 100%.

EXAMPLE 3

5 kg. of α-isophorone, 9 g of phosphomolybdic acid, 8 g. of copper sulfate.5H$_2$O and 2 g. of molybdenum-(VI)-oxide (molybdenum trioxide) in a 10 liter sulfonation flask provided with a stirrer, gas delivery frit, thermometer and reflux condenser are heated to 80°C. in an oil bath with continuous stirring. 12 liters of air per minute are continuously blown through the glass frit into the mixture. The temperature is maintained at 100°C. by means of thermostats. The initially dark green solution takes on a darker color during the course of several hours and shows a slightly increased viscosity.

After an oxidation time of 8 hours, 83% of the starting material is converted.

The mixture is smoothly distilled under reduced pressure to give 3954 g. of a yellow distillate which, apart from volatile and unknown oxidation products, contains mainly ketoisophorone. The yield of ketoisophorone amounts to 2768 g. (70%) and of isophorone 910 g. (23%).

The chemical yield amounts to 61% based on the reacted isophorone.

The crude product can be purified by fractional distillation or by crystallization from n-hexane.

EXAMPLE 4

Analogous results are obtained when 2500 g. of α-isophorone are oxidized in the presence of a catalyst consisting of 40 g. of phosphomolybdic acid, 5 g. of copper sulfate.5H$_2$O and 5 g. of silicomolybdic acid.

We claim:

1. A process for the preparation of ketoisophorone which process comprises oxidizing α-isophorone with an oxygen-containing gas in the presence of from about 0.1 to about 10 wt. percent based on the weight of said α-isophorone, of a catalyst selected from the group consisting of phosphomolybdic acid of or salt thereof, silicomolybdic acid or a salt thereof, molybdenum VI dioxybisacetylacetonate, vanadium IV dichlorobisacetylacetonate or vanadium V oxy-dichloromonoacetylacetonate, said oxidation being carried out in the presence or absence of solvent at a temperature of from about 50°C. to 150°C.

2. A process according to claim 1 wherein a catalyst additive selected from the group consisting of copper (II) salt, cer-(III)-acetylacetonate, molybdenum trioxide, palladium, an alkali metal dichromate and tungstic acid is employed, said additive being present in an amount of from about 2 wt. percent to about 50 wt. percent based on the total amount of catalyst.

3. A process according to claim 2 wherein said catalyst additive is present in an amount of from about 2 wt.% to about 20 wt.% based on the total amount of catalyst.

4. A process according to claim 1 wherein air is used as the oxygen-containing gas.

5. A process according to claim 1 wherein the oxidation is carried out in the absence of a solvent.

6. A process according to claim 1 wherein the oxidation is carried out in the presence of an inert solvent.

7. A process according to claim 6 wherein said inert solvent is a halogenated or alkylated aromatic solvent.

8. A process according to claim 1 wherein the oxidation is carried out at a temperature of about 80°–100°C.

9. A process according to claim 1 wherein the catalyst is used in an amount of about 0.5–4 wt.% based on the α-isophorone used.

10. A process according to claim 9 wherein the catalyst is used in an amount of about 2 wt.% based on the α-isophorone used.

* * * * *

UNITED STATES PATENT AND TRADEMARK OFFICE
CERTIFICATE OF CORRECTION

PATENT NO. : 3,960,966
DATED : June 1, 1976
INVENTOR(S) : ERICH WIDMER AND MARCEL SEURET It is certified that error appears in the above-identified patent and that said Letters Patent are hereby corrected as shown below:

Claim 1, column 4, line 9 -

"acid of or salt"   should be

-- acid or a salt --.

Signed and Sealed this

Fifth Day of April 1977

[SEAL]

Attest:

RUTH C. MASON
Attesting Officer

C. MARSHALL DANN
Commissioner of Patents and Trademarks